(12) United States Patent
Callahan

(10) Patent No.: US 6,416,328 B1
(45) Date of Patent: Jul. 9, 2002

(54) INTERCONNECTIVE AND INTERRELATIONAL INFORMATION INTERFACE SYSTEM

(76) Inventor: John F. Callahan, 2513 W. Peterson Ave., Chicago, IL (US) 60659

( * ) Notice: Subject to any disclaimer, the term of this patent is extended or adjusted under 35 U.S.C. 154(b) by 0 days.

(21) Appl. No.: 09/361,007

(22) Filed: Jul. 27, 1999

Related U.S. Application Data

(60) Provisional application No. 60/094,608, filed on Jul. 30, 1998.

(51) Int. Cl.[7] ............................ G09B 19/00; G06F 17/60
(52) U.S. Cl. .................... 434/322; 434/219; 434/307 R; 705/2
(58) Field of Search ................................ 434/118, 236, 434/350, 219; 705/2

(56) References Cited

U.S. PATENT DOCUMENTS

| | | | | |
|---|---|---|---|---|
| 4,803,039 A | * | 2/1989 | Impink, Jr. et al. | 376/216 |
| 5,727,950 A | * | 3/1998 | Cook et al. | 434/350 |
| 5,829,983 A | * | 11/1998 | Koyama et al. | 434/118 |
| 5,884,272 A | * | 3/1999 | Walker et al. | 705/1 |
| 5,911,581 A | * | 6/1999 | Reynolds et al. | 434/236 |
| 5,954,510 A | * | 9/1999 | Merrill et al. | 434/236 |
| 5,961,332 A | * | 10/1999 | Joao | 434/236 |
| 6,033,226 A | * | 3/2000 | Bullen | 434/219 |
| 6,157,808 A | * | 12/2000 | Hollingsworth | 434/350 |
| 6,162,060 A | * | 12/2000 | Richard et al. | 434/118 |

* cited by examiner

*Primary Examiner*—Joe H. Cheng
*Assistant Examiner*—Kathleen M. Christman
(74) *Attorney, Agent, or Firm*—Factor & Partners, PLC

(57) ABSTRACT

An interconnective and interrelational information system comprising at least one computer having an input member, an output member and an storage member. At least one of the at least one computers includes a managing structure, a data storage structure and a training structure. The managing structure manages at least one process. The data storage structure is associated with the process managing structure, and includes at least one item of data pertaining to the at least one process. The training structure facilitates the training of at least one employee to complete the processes identified in the process managing structure. The training structure interfaces with the process managing structure and with the data storage structure, to, in turn, obtain the necessary item of data from the data storage structure to provide training to the at least one employee for the at least one process. The invention further includes methods of managing processes and training employees.

18 Claims, 2 Drawing Sheets

INTERCONNECTIVE AND INTERRELATIONAL INFORMATION INTERFACE SYSTEM

This Application claims the benefit of U.S. Provisional Patent Application, Ser. No. 60/094,608 filed Jul. 30, 1998.

BACKGROUND OF THE INVENTION

1. Field of the Invention

The invention is directed to a control system for various types of operations, organizations and entities, and more particularly, to a synergistic, multi-dimensional system to organize, monitor, control and document complex, multi-faceted organizational activities, including task management and personnel training.

2. Background Art

The need for organization systems for large business and organizations has long been known in the art. In particular, such has been known for healthcare providers. It will be understood that the invention is not limited to that particular field, and, in fact, the system has application in other industries, including computer programming, auto repair centers, law firms, to name just a few. With respect to the healthcare industry, the Federal Government has developed many guidelines, rules, regulations and procedures with which healthcare providers must comply. To fully comply, a system of training, follow-up and management should be instituted by the healthcare provider. Currently, healthcare providers provide some on-site training of groups of employees, generally upon initiation of employment, and at best maintain a set of training manuals and compliance manuals. However, this industry (like other industries), due in part to new regulations and required procedures, as well as evolving processes and employee turnover, is not well suited to such passive training and monitoring. As a result, many healthcare providers find themselves with processes that remain incomplete, leading to monetary loss for failure to comply with the necessary procedures and with a labor force that is not equipped/trained to properly and fully execute with the necessary procedures, and to properly administer the organization. Additionally, the labor force is hard to retrain as new requirements issue, or as problems are spotted.

It is therefore an object of the invention to provide a system that is both interconnective and interactive, which can implement a process based system to facilitate full compliance with and performance of desired processes.

It is a further object of the invention to facilitate modifications in employees, employment processes, and controls on an interactive basis, to adapt to an ever changing environment, which may involve constant introduction of new processes and procedures.

It is further an object of the invention to facilitate training of employees, wherein the employee dynamically receives the necessary training and the necessary updating to the initial training.

As explained above, the system is capable of use in a multitude of environments, and is not limited to a particular industry or a particular group of industries.

SUMMARY OF THE INVENTION

The invention comprises an interconnective and interrelational information system comprising at least one computer having input means, output means and storage means. At least one of the at least one computers further includes managing means, data storage means and training means. The managing means manages the at least one process. The data storage means is associated with the process managing means, and includes at least one item of data pertaining to the at least one process. The training means facilitates the training of at least one employee to complete the processes identified in the process managing means. The training means interfaces with the process managing means and with the data storage means, to, in turn, obtain the necessary item of data from the data storage means to provide training to the at least one employee for the at least one process.

In one embodiment, the system includes means for tracking procedures which interfaces with the process managing means and the employee training means. The procedure tracking means includes at least one procedure to complete the at least one process. In one embodiment, the procedure tracking means includes a plurality of procedures required for the completion of the at least one process.

In another such embodiment, the at least one process comprises a plurality of processes. The procedure tracking means includes a plurality of procedures required to complete each of the plurality of processes. In certain embodiments, certain procedures may be applicable to a variety of processes.

In another embodiment, the invention further includes means for tracking outside contractors. The outside contractor tracking means is associated with at least one of the process managing means, the storage means and the training means. The contractor tracking means providing outside contractors with a predetermined desired level of access to the foregoing means. As a result, outside contractors are integrated into the system.

In one embodiment, the at least one computer comprises a plurality of computers which are linked by way of a network. In one such embodiment, the network comprises the Internet.

In one preferred embodiment, the process manager means further includes means for alerting at least one individual responsible for the execution of at least a portion of the process upon the presence of a predetermined condition. In one such embodiment, each of the at least one process includes at least one of a start/completion date, objective and performance goal. The predetermined condition of the alert means comprises the failure to comply with at least one of the start/completion date, objective and performance goal.

In another such embodiment, the alert means further includes means for employee communication with the process managing means, to, in turn, facilitate communication with the process managing means relative to the at least one process. In one such embodiment, the communication means comprises e-mail communication means. In another such embodiment, the communication means includes means for preserving the anonymity of the employee communication means.

In another embodiment, the data storage means includes means for storing at least one of the group consisting of: audio, visual, textual and multi-media data.

In a preferred embodiment, the training means further includes means for coordinating the desired training for at least one employee and means for presenting the training to the at least one employee. The coordinating means is associated with the procedure means and the storage means, and, interfaces with each of these means to coordinate training for at least one employee. The training presenting means is associated with the coordinating means and the data storage means.

In such an embodiment, the at least one employee comprises a plurality of employees. The coordinating means further includes means for tracking the plurality of employees. The plurality of employees can further be tracked as to at least one of employee name, start dates, training received and dates of the training.

In another such embodiment, the training means further includes means for classifying employment positions associated with the coordinating means. The employment position classification means comprises a listing of employment positions and training modules necessary for each such employment position, to, in turn, facilitate tracing of the at least one employee.

In another preferred embodiment, the system is utilized in association with a compliance program for a health care facility.

The invention further includes a method of training at least one employee to complete at least one process. The method comprises the steps of: (a) providing at least one process from the process managing means; (b) providing the means for storing data pertaining to training for the process; (c) coordinating the storage means with the at least one process, to, in turn, develop a training program for the employee; and (d) providing training to the at least one employee.

The invention further includes a method of managing at least one process. The method comprises the steps of: (a) providing a process in process managing means; (b) providing means for storing data pertaining to the process; (c) interfacing the data storage means with the process managing means; (d) developing a set of procedures for completing the process; and (e) facilitating entry by a user a record as to the completion of the at least one process.

In a preferred embodiment, the method further comprises the step of training at least one employee to complete the process.

In another preferred embodiment, the method comprises the step of alerting a responsible individual if the at least one process is not completed by a predetermined desired date.

DETAILED DESCRIPTION OF THE DRAWINGS

Figure 1:
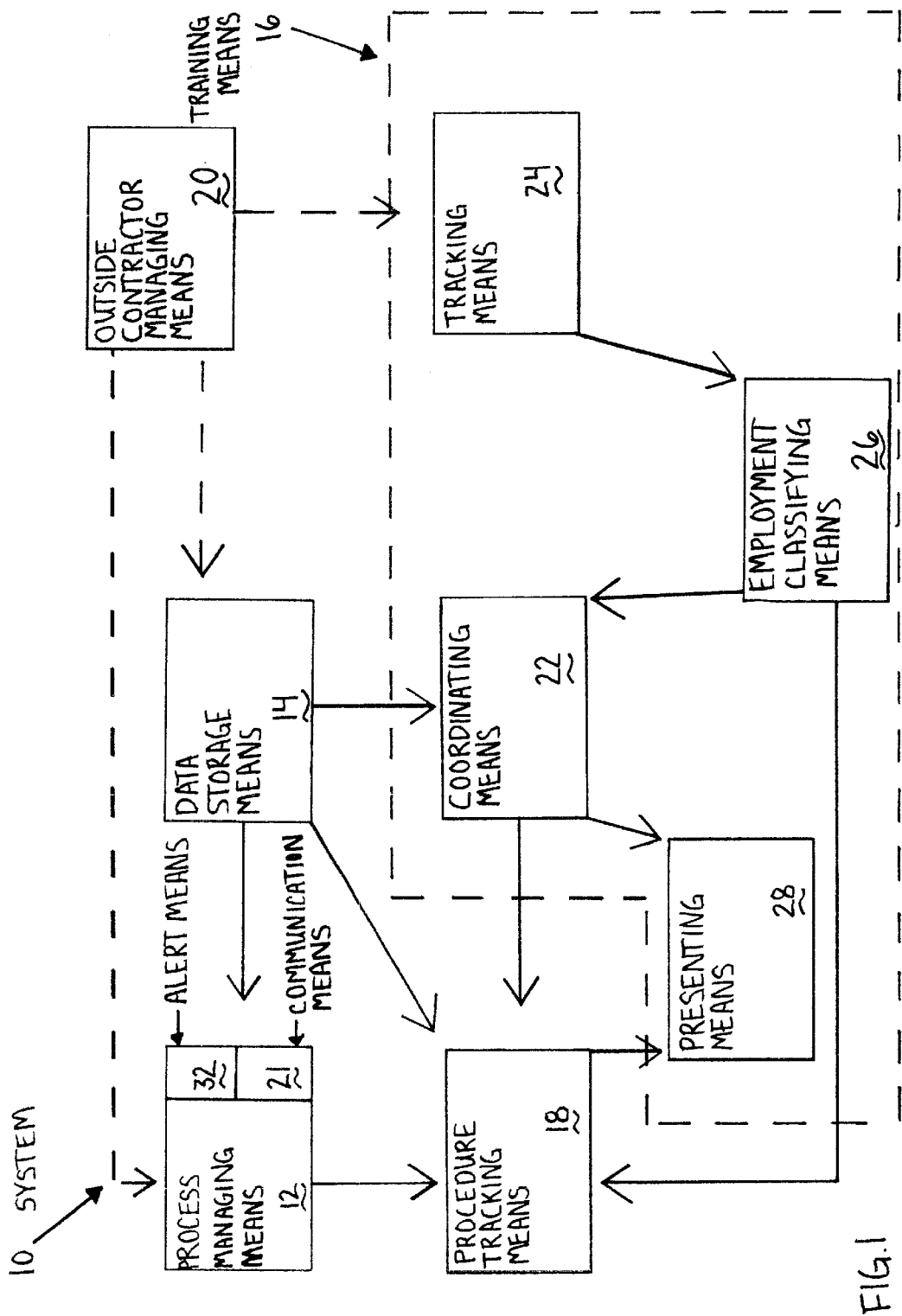
FIG. 1 of the drawings is a schematic of the system of the present invention.

While this invention is susceptible to embodiment in many different forms, there is shown in the drawings and will be described below in detail, a specific embodiment with the understanding that the embodiment is to be considered to be an exemplification of the principles of the invention, and the embodiment is not intended to limit the invention to the embodiment illustrated.

As shown in FIG. 1, the interconnective administration system 10 comprises means 12 for managing processes, means 14 for storing data, means 16 for training, means 18 for tracking procedures and means 20 for tracking outside contractors. The administrative system is designed to be dynamic and to be administered and operated through a suitable network of computers, including, local area networks and wide area networks, among others. While various systems are contemplated, it is preferable that the system be maintained on a servers, some of which are SQL based and which servers are preferably accessible by way of the Internet. As a web based system, the users have the ability to interface with the system from any computer which has access to the world wide web. Of course, proper safeguards and firewalls can be built into the access so as to facilitate access to a predetermined group of individuals.

Figure 2:
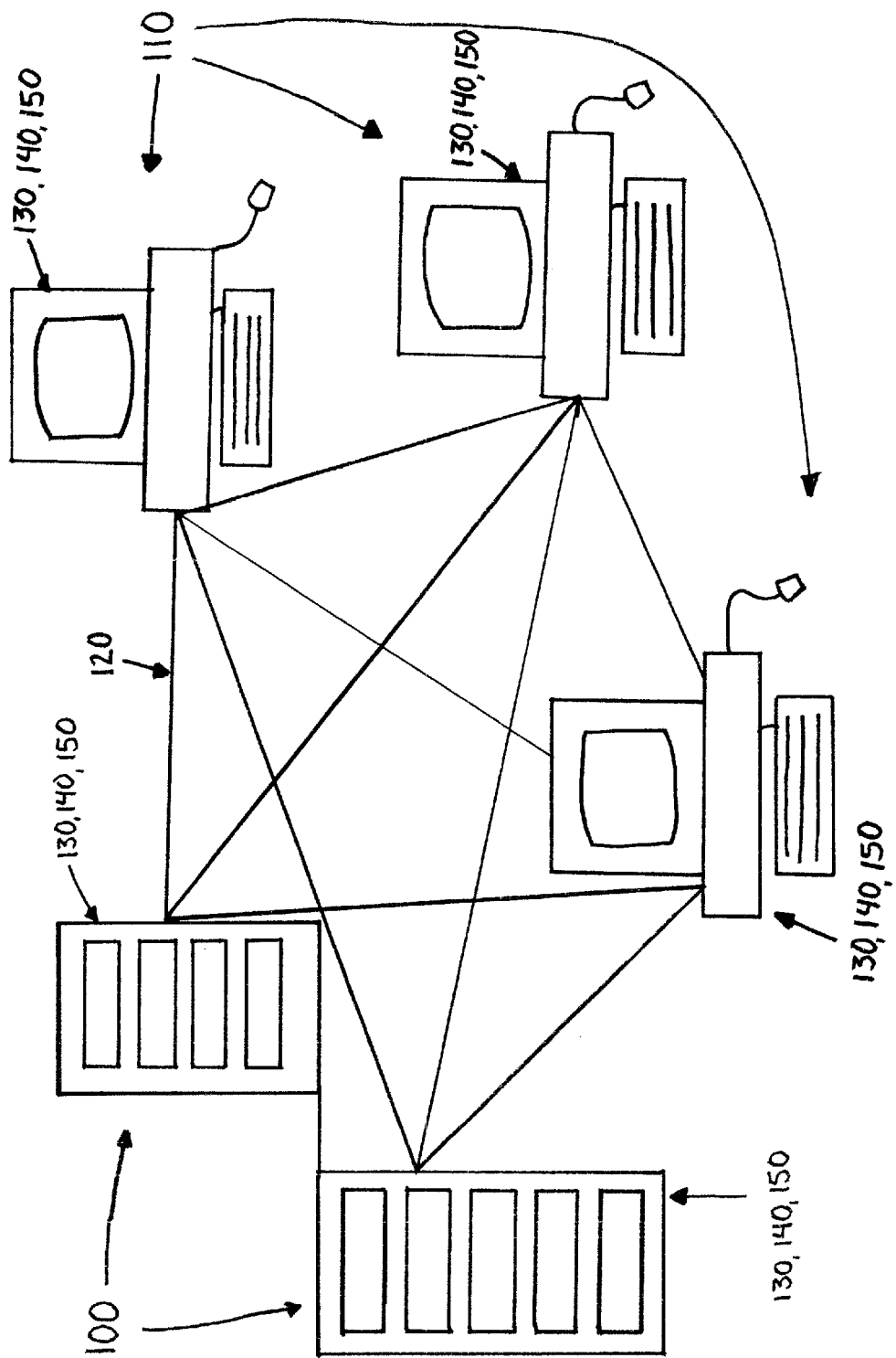
FIG. 2 of the drawings is a schematic of the network over which the system may operate.

A suitable system is shown in FIG. 2 wherein server computers 100 are associated with terminal computers 110 via network 120 (such as a LAN, WAN or Internet). Of course, the number and type of servers and terminals (clients) and the particular means of communication (such as by Internet) will be understood by those having skill in the art.

Each such computer generally includes input means 130, output means 140 and storage means 150. The input means may comprise, a keyboard, a NIC card, a SCSI/IDE interface, mouse, among others. The output means may comprise a monitor, a counter, a NIC card, SCSI/IDE interface, among others. The storage means may comprise any number of hard drives, optical drives, CD Rom drives, RAM, ROM, as well as other data storage device.

Process managing means 12 maintains a comprehensive listing of the processes that must be performed to complete or achieve a desired objective, or to maintain an ongoing process. Information that is managed for each process includes, among others, start dates, completion dates, objectives and performance goals. Process managing means 12 includes a vehicle by which the managed information may be entered by the appropriate employees or operators and the process managing means is associated with the data input means for purposes of receiving information with respect to the various processes that are required. For example, the process managing means is capable of accessing the completion or status of each process in the system. Thus, as will be explained below, users are capable of entering into the process managing means the completion of a process, the further work on a process. In addition, the process managing means through alert means or other notification procedure can notify anyone in the system as to the progress, completion, problems with, or the failure to complete any process or portion of a process. It is contemplated that much of the progress and status reports as to any process and the completion/operation of same can be communicated to responsible individuals via e-mail, a paging system, textual messaging, or paper generating messaging. The programming of suitable software for use with the process managing means will be understood by one having skill in the programming art.

Through the monitoring of completion dates and performance goals, the process managing means includes alert means 32 which is triggered by a failure to meet any one or more of start/completion dates, objectives and performance goals. The alert means may be configured to alert the desired (or in some instances the required) personnel or departments in the managerial structure. For example, the alert means may operate by automatically sending an e-mail or other message to the individual who is responsible for the completion of any necessary process.

Communicating means 21 is associated with alert means 32 and provides a communication link for employees, contractors and others to inform management (or anyone who in a position of responsibility) as to various issues. For example, such communication could comprise a complaint, a perceived or possible violation of the required standards, regulations or procedures, or even a suggestion as to performance improvement or as to another issue. To utilize such a system, a message can be registered with the communication means by way of completing and submitting a violation form. The form is then keyed into a computer which triggers an alarm with one of the responsible individuals. The reports can be given anonymously, thereby negating any possible instances of retribution.

It is likewise contemplated that the messages can be made via an anonymous e-mail message system. For example, terminals at the facility can have the ability to send e-mail messages to management on an anonymous basis. In one embodiment, the e-mail is printed out at the terminal as well, and given a unique numerical identifier. The employee can keep the copy of the e-mail for future reference, and, the numerical identifier provides a means for tracking the message. It is likewise contemplated that the employee can, in the e-mail communication, identify his or her name. In sum, if the user has any issues, the user can immediately write an unsigned/untraceable e-mail to a responsible management individual. Once management is informed, management can then decide as to the proper course of action.

Means 16 for storing data comprises a database of information which is capable of retaining, retrieving and sending the information, in many forms and formats, including audio/visual, textual, multi-media, etc. The information annotates, explains, documents, enhances or otherwise is relevant to, or pertains to, any of the required processes dictated by process managing means 12. For example, and certainly not limited to the following, the data storing means may include operating procedures, standards of conduct, regulations, interpretations, current journal/industry literature, suggestions, tips, hints, among others. The data storing means is associated with the process managing means and data can be accessed by employees/users who require information so as to be able to complete a process. In particular, the process managing means includes means for searching (such as through a word or phrase search) the data storage means, which, in turn, facilitates the obtaining of information from the data storage means by a compliance officer or other employee who is trying to obtain information relating to a process.

As will be explained, the data storing means is likewise accessible by the contractor managing means, the procedure means and the training means. A control mechanism for the level of access and the right to receive information from the data storing means may be incorporated into the data storage means, for security purposes. In particular, access to the system is available to authorized individuals through a login/password "key", which can provide individualized levels of access to each individual. Specifically, certain individuals would be given access to the procedure manual, but they would not be given access to the process manager or training modules. Others will have the ability to add data files, while others can make changes to data files, while still others can only read data files. Generally, it is contemplated that virtually any individual has access to the communication means, and, therefore, anyone can send messages to responsible individuals on virtually any issue. The particular security system that is chosen, and the particular security measures are known to those with ordinary skill in the art of computer access security.

Training means 16 comprises means 24 for tracking employees, means 26 for classifying employment positions, means 22 for coordinating the desired training, and means 28 for presenting training materials to employees. Together, the different components of training means 16 provide the continued and necessary level of training on an individual employee basis, so that all of the employees maintain the proper level of training for the particular employment position and for the completion of the required processes—even as new procedures and requirements are presented.

In particular, employee tracking means 24 maintains an exhaustive list of all desired employees. In a healthcare provider environment, this may include each and every employee including, but not limited to, doctors, administrators, nurses, therapists, janitors, maintenance engineers, among others. Such information included with each employee would include start dates, any training attended and received, and dates of such training. Employment position classification means 26 comprises an index of files and training modules (all of which files and modules are contained in the data storage means 16) as they pertain to the certain employment positions. In particular, such training modules and files indexed with any particular employment position comprise those materials management considers necessary (or otherwise required, through, for example, government regulations) for optimal completion of, or employee understanding of, processes, expectations and/or requirements. It will be understood that employee tracking means may be implemented through development of a computer software package programmed by one of skill in the computer programming art.

Training coordinating means 22 comprises a unit which references the employee tracking means 24 and employment position classification means 26 to determine, and to coordinate, the particular training required for each individual employee. The factors which require consideration when complying necessary training schedules include, among others, the training the employee has already received, the starting dates of the employee, the last training dates, the requirements of the position, any changes that may have occurred during since the last training, and any disabilities, restrictions or special needs of the employee. Thus, at any moment, it can be determined what training, if any, is required for any particular employee, and, when the training can be administered.

When additional training is required, the training coordinating means 22 interfaces with data storage means 14 to provide the necessary training via the material presenting means 28. Specifically, material presenting means 28 may comprise any number of training tools which draw information from data storage means 14, as directed by training coordinating means 22. Material presenting means 28 may comprise audio-visual, multimedia, live lecture, printed documentation, computer related training, among other training media formats. It is contemplated that the materials presenting means 28 may operate over the internet, thus allowing access by way of virtually any computer attached to the internet by a trainee. In addition, it is contemplated that the tracking may be in virtually any language, so that employees can be trained and can be retrained in their native language. Moreover, it is contemplated that the training means may include other means for adapting training to a particular employee, if, for example, the particular employee has special needs or special requirements. In this manner, the system can facilitate training of virtually any individual. Once the training is complete, training coordinating means 22 directs employment tracking means 24 to update the employee's records so as to indicate that the additional training has been completed.

Procedure tracking means 18 is associated with storage means 14 and process managing means 12. The procedure tracking means coordinates with data storage means 14 and the process managing means 12 to develop a detailed procedure for the completion of processes, all based upon data and information received from the data storage means.

The procedure tracking means may be accessed by any employee to review the necessary procedures in order to complete a process, or by management to determine the complexity or manpower necessary to complete certain processes. Further, procedure tracking means 18 interfaces with material presentation means 28 to provide the necessary information in any desired media.

Contractor management means 20 permits interaction of the system with outside contractors and/or non-employee workers. These contractors are capable of interfacing with the process management means, the data storage means and the training means, so that the outside contractor is capable of reporting completed processes, obtaining information necessary to complete the processes and obtaining the necessary training to complete the processes. In addition, the process managing means can likewise track the performance of the contractors, as can be done with the employees.

The operation of the system is described below relative to the healthcare provider industry, with the understanding that it is equally adaptable for use in a multitude of other environments and industries. In particular, in such an industry, data storage means 12 includes, among many other things, data relating to different regulations that must be followed, the guidelines relative to all facets of the healthcare industry, journals/texts regarding all types of healthcare issues, etc. As explained above, training means 16, through employee tracking means 24, maintains much information regarding all employees. In addition, all of the employment qualifications and requirements for each healthcare provider employee position are maintained by employment position classification means 26 of training means 14. Accordingly, on a dynamic basis, as new regulations or procedures are introduced into the data storage means, coordination means 22 of training means 16 interfaces with data storage means 14 to determine which employees require additional training. Subsequently, the proper and desired material can be prepared and transmitted through the material presenting means 28 and the employees can be properly trained.

Likewise, through contractor management means 20, contractors to the healthcare provider similarly interface with the training means such it is likewise possible to train and continue training, on a dynamic basis, any and all contractors which are performing processes and procedures for the provider on a contractor basis. This could include, for example, maintenance or janitorial crews, as well as doctors.

Once the desired employees are all entered into the system, and the desired employees have been trained to execute the required processes, the employees can refer to the process means to determine the required processes that must be completed and the required dates of completion of each of these processes. To assist with the completion of processes, the employees may reference the procedure tracking means or the data storage means to determine the necessary steps that must be taken to complete the requisite processes and the means by which to undertake the necessary steps.

Once each process is completed, process managing means 12 is informed of the completion of the required processes. The process managing means records the date of the completion of the process as well as the identification of employees/contractors that have completed the processes. At any time healthcare compliance officers can review, through the process managing means, a record which indicates each and every process in the system that has been undertaken and completed. In addition, the compliance officer or other employee can access the content of the storage means and search the records of the storage means to discover further information relative to any particular process.

As explained above, in a situation where a process has not been completed within the allotted or set time constraints, the process managing means is capable of alerting the necessary individuals (such as healthcare compliance officers) that the process is not complete, to, in turn, insure that the situation is corrected and that the process is subsequently complete quickly. The alert means can be set up so that it alerts any one of a number of individuals, such as the employee who is to complete the process, the team responsible for completing the process, as well as healthcare compliance officers and other management, as desired. In addition, several levels of alerting may be available, depending on the severity of the incomplete process. Moreover, process managing means 12 can likewise serve other functions, such as utilizing the data to determine whether or not a bottleneck exists with respect to certain processes, or whether certain problems exist with respect to certain teams or certain employees (such as poor work effort, lack of proper training, etc.). This feedback can help modify the training or the operation of the processes, and can provide a mechanism by which to quantify an employee's progress. Such analysis will likewise result in an improved and better managed healthcare provider.

Any time that a regulation in the healthcare industry is introduced or an old regulation is amended, and entered into data storage means 14, it can instantly be interfaced and interconnected with process managing means 12 and training means 16 so that, if new processes result from the regulation changes, the proper individuals can be trained through the training means to accomplish these processes, and little time is lost between introduction of new processes to the system and the implementation and, in turn, completion of same.

In summary, the invention provides a system in which to recognize and monitor all processes to be performed, which, in turn, facilitates the assessment and control of the performance of these processes in a timely manner. This assessment allows management to evaluate the effects of the level of performance of one process on other processes and/or the task as a whole, and, to dynamically make changes to the procedures. The system likewise provides continued training and education, and constantly can update, retrain or continue to train individuals as new requirements/processes are determined by the training means.

The foregoing description and drawings merely explain and illustrate the invention, and the invention is not limited thereto, as those skilled in the art who have the disclosure before them will be able to make modifications and variations to the system without departing from the scope of the invention.

What is claimed is:

1. A computer program product for facilitating compliance by a facility with a plurality of regulations comprising:
 a computer data storage device; and
 computer program instructions, recorded on the computer data storage device, executable by a computer processor, for performing the steps of:
  storing data pertaining to at least one process;
  identifying at least one process which requires completion for compliance with a plurality of regulations;
  determining at least one procedure necessary to complete the process;
  assigning the execution of at least one procedure to at least one person;

determining the training necessary for the at least one person to complete the execution of the procedures;

determining if the at least one person has completed the determined necessary training;

providing the determined necessary training to the at least one person if it is determined that the at least one person has not completed the determined necessary training;

facilitating the updating of the progress of the at least one person relative to the completion of the process; and monitoring the progress of the at least one person relative to the completion of the process, to, in turn, determine compliance by a facility with the plurality of regulations.

2. The product of claim 1 further comprising the step of:

alerting at least one other person in the event that the step of monitoring determines that the completion of the process is not proceeding as necessary for the compliance by a facility with the plurality of regulations.

3. The product of claim 1 wherein the step of storing data pertaining to a process further comprises the steps of:

storing data pertaining to each procedure required to complete the at least one process; and storing data pertaining to training for each procedure required to complete the at least one process.

4. The product of claim 1 wherein the step of assigning firer comprises the steps of:

storing data pertaining to the at least one person, the data including:
name;
job description; and
skills; and identifying at least one person from the stored data having at least one skill for completing at least one procedure of the at least one process.

5. The product of claim 4 wherein the step of determining the training further comprises the step of:

updating the stored data pertaining to the at least one person after the step of providing the necessary training to the at least one person.

6. The product of claim 1 wherein the step of facilitating the updating further comprises the step of facilitating the updating of the progress by the at least one person.

7. The apparatus of claim 1 wherein the computer program instructions further performs the step of:

providing a facilitating means for the at least one person to communicate with at least one other person.

8. The apparatus of claim 7 wherein the step of providing a facilitating means further comprises the step of:

preserving the anonymity of the at least one person.

9. The apparatus of claim 7 wherein the step of providing a facilitating means further comprises the step of:

facilitating email communication between the at least one person and the at least one other person.

10. A computer program product for facilitating compliance by a facility with a plurality of regulations comprising:

a computer data storage device; and computer program instructions, recorded on the computer data storage device, executable by a computer processor, for performing the steps of:

storing data pertaining to a plurality of processes necessary for compliance with a plurality of regulations;

identifying processes on an ongoing basis which require completion for compliance with a plurality of regulations, for each such identified process completing the steps of:

determining at least one procedure necessary to complete the process;

assigning the execution of each at least one procedure to at least one person;

determining the training necessary for each at least one person to complete the execution of each at least one procedure;

determining if the at least one person has completed the determined necessary training;

providing the determined necessary training to the at least one person if it is determined that the at least one person has not completed the determined necessary training;

facilitating the updating of the progress of each at least one person relative to the completion of the process; and monitoring the progress of each at least one person relative to the completion of the process, to, in turn, determine compliance by a facility with the plurality of regulations.

11. The product of claim 10 further comprising the step of:

analyzing the progress of the completion of a process.

12. The product of claim 10 further comprising the step of:

updating the data pertaining to the plurality of processes necessary for compliance with a plurality of regulations on an ongoing basis.

13. The product of claim 10 further comprising the steps of:

storing data pertaining to each at least one person, the data including job description and trained skills;

periodically reviewing the training skill data and job description data pertaining to each at least one person;

determining if any further training is necessary for each at least one person; and training each at least one person if the step of determining results in a finding that training is necessary.

14. The product of claim 10 further comprising the step of:

alerting at least one person in the event that the step of monitoring determines that the completion of any process is not proceeding as necessary for the compliance by a facility with the plurality of regulations.

15. The product of claim 14 further comprising the step of:

alerting at least one person other than the person that was previously alerted in the event that the step of monitoring determines that the completion of the process is not proceeding as necessary for the compliance by a facility with the plurality of regulations after the first step of alerting.

16. The apparatus of claim 10 wherein the computer program instructions further performs the step of:

providing a facilitating means for the at least one person to communicate with at least one supervisor.

17. The apparatus of claim 16 wherein the step of providing a facilitating means further comprises the step of:

preserving the anonymity of the at least one person.

18. The apparatus of claim 16 wherein the step of providing a facilitating means further comprises the step of:

facilitating email communication between the at least one person and the at least one other person.

* * * * *